United States Patent [19]

Uemura et al.

[11] 4,421,845
[45] Dec. 20, 1983

[54] SILVER HALIDE PHOTOGRAPHIC LIGHT-SENSITIVE MATERIAL

[75] Inventors: Morito Uemura, Hino; Kenichi Kishi, Sagamihara; Satoshi Nakagawa, Hino; Shuji Kida; Hiroshi Sugita, both of Hachioji, all of Japan

[73] Assignee: Konishiroku Photo Industry Co., Ltd., Japan

[21] Appl. No.: 357,149

[22] Filed: Mar. 11, 1982

[30] Foreign Application Priority Data

Mar. 19, 1981 [JP] Japan ................................. 56-39766

[51] Int. Cl.³ .............................................. G03C 1/40
[52] U.S. Cl. .................................... 430/544; 430/543; 430/553; 430/555; 430/557; 430/558; 430/559; 430/566
[58] Field of Search ............... 430/542, 543, 544, 550, 430/551, 558, 564, 566, 570, 597, 598, 599, 607, 559, 553, 555, 557

[56] References Cited

U.S. PATENT DOCUMENTS

| | | | |
|---|---|---|---|
| 4,062,683 | 12/1977 | Monbaliu et al. | 430/558 |
| 4,130,427 | 12/1978 | Monbaliu et al. | 430/558 |
| 4,283,472 | 8/1981 | Gompf et al. | 430/558 |
| 4,308,343 | 12/1981 | Ichijima et al. | 430/558 |
| 4,310,618 | 1/1982 | Fernandez et al. | 430/558 |

Primary Examiner—J. Travis Brown

[57] ABSTRACT

A silver halide photographic light-sensitive material which comprises at least one of those pyrazole compounds represented by the following general formula:

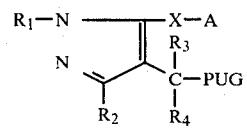

wherein A is a group which can be eliminated in a photographic process condition; X is

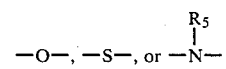

wherein $R_5$ is a hydrogen atom or an alkyl, an aryl, an acyl or a sulfone group, which $R_5$ group may combine together with $R_1$ to form a condensed ring; $R_1$ is a hydrogen atom or an alkyl, an aryl, an acyl, a sulfone, an alkoxy, or a heterocyclic residue; $R_2$ is a hydrogen atom or an alkyl, an aryl, an alkoxy, an amino, an acid amide, a sulfonamide, a carboxyl, an alkoxycarbonyl, a carbamoyl, a cyano, or a halogenated alkyl group, $R_3$ and $R_4$ each is a hydrogen atom or an alkyl or an aryl group; and PUG is a photographically useful group which is released after elimination of the A group in a photographic processing condition and which has a hetero atom directly combined with the carbon substituted in the fourth position of the pyrazole nucleus.

6 Claims, No Drawings

SILVER HALIDE PHOTOGRAPHIC LIGHT-SENSITIVE MATERIAL

The present invention relates to a silver halide photographic light-sensitive material containing a protected, photographically useful compound.

Photographic additives, particularly those which react at the time of processing, may bring about undesirable side reactions or unacceptable photographic results when added as they are to a light-sensitive material. The addition of such additives in the form of being protected to improve the above disadvantage, i.e., in the form of precursors, not only minimize the undesirable influence upon the material prior to processing but enable to provide such an effect that the release therefrom can be effected corresponding to the passage of processing time. Further the release may be effected in the processed region only; in other words, they can be used in the condition that additives can act imagewise. DIR couplers disclosed in U.S. Pat. No. 3,148,062 and No. 3,227,554 are based on this idea. However, these techniques are those which merely protect additives or which involve the condensation in the position where substitution can be carried out by the coupling reaction of a coupler with the oxidant of a color developing agent, and it is difficult to obtain by these techniques DIR couplers excellent in both the desired releasing rate and the stability in storage.

As one of techniques to improve these disadvantages, disclosures have been made which are such that a linking group is provided between a protective group or a coupler and an additive, a photographically useful material, whereby their respective maximum functions can be displayed; for example, to improve the foregoing problems, Japanese Patent Examined Publication No. 39727/1979 discloses providing therebetween a linking group that forms quinonemethyd or naphthoquinonemethyd, while Japanese Patent Publication Open to Public Inspection (hereinafter referred to as Japanese Patent O.P.I. Publication) No. 145135/1979 and No. 53330/1980 disclose the providing therebetween of a linking group that brings about an intramolecular nucleophilic substitution reaction.

The present invention relates to these linking groups and the object of the invention is to provide a compound which plays the role of combining stably a protective group or a coupler with a photographically useful material, which combination releases at a desired rate the photographically useful material in a given processing condition and is improved in the stability in storage.

We have found that the above-described object can be attained by a silver halide photographic light-sensitive material comprising at least one of those pyrazole compounds having the formula:

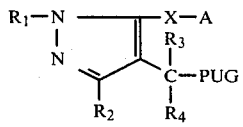

wherein A is a group that can be eliminated in a photographic processing condition: X is

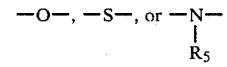

wherein $R_5$ is hydrogen atom, an alkyl, an aryl, an acyl, or a sulfone group, the $R_5$ being allowed to form a condensed ring together with $R_1$; $R_1$ is a hydrogen atom, an alkyl, an aryl, an acyl, a sulfone, an alkoxy, or a heterocyclic residue; $R_2$ is hydrogen, an alkyl, an aryl, an alkoxy, an amino, an acid amide, a sulfonamide, a carboxyl, an alkoxycarbonyl, a carbamoyl, a cyano, or a halogenated alkyl group; $R_3$ and $R_4$ each is hydrogen atom, an alkyl or an aryl group; and PUG is a photographically useful group combined through a hetero atom with the carbon atom substituted in the fourth position of the pyrazole nucleus.

Alkyl groups represented by the $R_1$, $R_2$, $R_3$, $R_4$ and $R_5$ in the above formula are preferably those having from 1 to 32 carbon atoms, which include, e.g., methyl, ethyl, n-propyl, iso-propyl, t-butyl, 2-ethyl-hexyl, 3,5,5-trimethyl-hexyl, n-octyl, t-octyl, n-dodecyl groups, and the like, and which also include these groups substituted by such groups as, e.g., alkoxy, aryloxy, cyano, alkylthio, arylthio, and the like.

Aryl groups represented by the $R_1$, $R_2$, $R_3$, $R_4$ and $R_5$ include phenyl and naphthyl, and those phenyl and naphthyl groups substituted by such substituents having from 1 to 5 carbon atoms as, e.g., alkyl, halogenated alkyl, halogen atoms, hydroxy, alkoxy, amino, acid amide, sulfonamide, carboxy, alkoxycarbonyl, acyl, carbamoyl, cyano, mercapto, alkylthio, sulfone, sulfo, nitro, sulfamoyl groups, and the like.

Acyl groups represented by the $R_1$ and $R_5$ have the formula

wherein $R_6$ is an alkyl or an aryl group.

Sulfone groups represented by the $R_1$ and $R_5$ have the formula $-SO_2-R_6$.

Heterocyclic residues represented by the $R_1$ include, e.g., furyl, pyranyl, imidazolyl, benzimidazolyl, pyrrolyl, pyrimidyl, triazinyl, thienyl, quinolyl, oxazolyl, benzoxazolyl, thiazolyl, benzthiazolyl groups, and the like.

Alkoxy groups represented by the $R_2$ have the formula $-O-R_7$ wherein $R_7$ is an alkyl group.

Amino groups represented by the $R_2$ have the formula

wherein $R_8$ and $R_9$ each is hydrogen or an alkyl group.

Acid amide groups represented by the $R_2$ have the formula $-NHCOR_6$; sulfonamide groups represented by the same have the formula $-NHSO_2R_6$; alkoxycarbonyl groups by the same have $-CO_2R_7$; carbamoyl groups by the same have

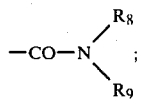

and halogenated alkyl groups by the same are those in which part of or all the hydrogen atoms of an alkyl are substituted by halogen atoms such as chlorine, bromine, fluorine, and the like.

Groups represented by the A in the formula that can be eliminated in a photographic processing condition are, to be more concrete, those which can be eliminated in an alkaline processing solution and which include hydrogen; such metals as sodium, potassium; alkali-hydrolyzable acyl and sulfonyl groups; those couplers whose bonding is made in the position where the oxidized color developing agent can be substituted; and those groups that can be eliminated by a redox reaction, particularly by being cross-oxidized with the oxidized color developing agent or by being reduced by a reducing agent such as hydroquinone.

Those represented by the PUG, to be more concrete, includes, e.g., reidues of development inhibitors, development accelerators, bleach restrainers, bleach accelerators, developing agent, fixers, silver halide solvents, silver-complex forming agents, hardeners, tanning agents, toning agents, fogging agents, antifoggants, chemical or optical sensitizers, desensitizers, photographic dyes or precursors thereof, and couplers such as competitive couplers, color couplers, DIR couplers.

One of these represented by the PUG is combined through the intramolecular hetero atom such as sulfur, oxygen, nitrogen, with the carbon substituted in the fourth position of the pyrazole nucleus.

These compounds of the present invention have the function that they release the PUG after the A is eliminated in a photographic processing condition. The degree of the release, although variable according to desire, is generally desirable to be controlled so that the release is carried out during the processing time for the light-sensitive material. The reaction mechanism that the PUG is not released until the A is eliminated is uncertain, although it is considered due to the fact that, for example, in the case where X is —O—, and the $R_3$ and $R_4$ each is hydrogen, the PUG is released through an intermediate such as pyrazolonemethyd.

The compounds of the present invention, by selecting a desired group as the A, may also be eliminated imagewise, for example, in a photographic condition. Further, by selecting desired groups as the X, PUG, and $R_1$ through $R_5$, respectively, the release of the photographically useful group at the most suitable rate may be carried out.

As an example, when such selection is applied to DIR couplers, very excellent effect may be produced, that is, in the case where a coupler residue is selected as the A, and a development inhibitor residue is selected as the PUG. The coupler is combined with the X in the position where the oxidized color developing agent may substitute by the coupling thereof. Such DIR couplers (hereinafter preferred to as "timing DIR") wherein a timing group as a linking group is interposed between the development inhibitor residue and the coupler residue are disclosed in the previously mentioned Japanese Patent O.P.I. Publication No. 145135/1979. However the timing DIRs described in this patent publication are of the type of releasing development inhibitors through an intramolecular nucleophilic substitution reaction and essentially different from the compounds of the present invention.

When the present invention is applied to the timing DIR, the selection of the most suitable compound for the light-sensitive material may be carried out by variously changing couplers as the A and development inhibitors as the X, $R_1$ through $R_5$ and PUG in the foregoing general formula. As examples of coupler residues represented by the A and the PUG in the formula there are such coupler residues as generally usable in color photographic light-sensitive materials.

For example, with respect to yellow coupler residues, there may be used the residues of benzoyl acetanilide type yellow couplers or of pivaloyl acetanilide type yellow couplers as described in U.S. Pat. No. 2,298,443, No. 2,407,210, No. 2,875,057, No. 3,048,194, No. 3,265,506, No. 3,447,928 and "Farbkuppler—eine Literaturübersicht" Agfa Mitteilung (Band II) pp. 112–126 (1961), and the like. With respect to magenta coupler residues, there may be used the residues of such various magenta couplers as pyrazolone magenta couplers, indazolone magenta couplers, and the like as described in U.S. Pat. No. 2,369,489, No. 2,343,703, No. 2,311,082, No. 2,600,788, No. 2,908,573, No. 3,062,653, No. 3,152,896, No. 3,519,429, and the above-mentioned Agfa Mitteilung (Band II) pp. 126–156 (1961), and the like.

And, with respect to cyan coupler residues, there may be used the residues of such naphthol or phenol couplers as described in U.S. Pat. No. 2,367,531, No. 2,423,730, No. 2,474,293, No. 2,772,162, No. 2,895,826, No. 3,002,836, No. 3,034,892, No. 3,041,236, and the above-mentioned Agfa Mitteilung (Band II) pp. 156–175 (1961), and the like.

In addition to these coupler residues, there may also be used the residues of such black dye forming couplers as described in West German OLS Patent No. 2,644,915.

On the other hand, those compounds reacting with the oxidized color-developing agents such as represented by cyclic carbonyl compounds but not forming any color-forming dyes may also be used as the compound of the present invention, and these compounds are described in U.S. Pat. No. 3,632,345, No. 3,928,041, No. 3,958,993, No. 3,961,959, and British Pat. No. 861,138.

Typical examples of development inhibitor residues of the present invention include residues of mercaptotetrazole, selenotetrazole, mercaptobenzothiazole, selenobenzothiazole, mercaptobenzoxazole, selenobenzoxazole, mercaptobenzimidazole, selenobenzimidazole, benzotriazole, and benzodiazole, as described in U.S. Pat. No. 3,227,554, No. 3,384,657, No. 3,615,506, No. 3,617,291, No. 3,733,201, and British Pat. No. 1,450,497.

The following are concrete examples of the compounds of the present invention, but the present invention is not limited thereto:

Exemplified Compounds:

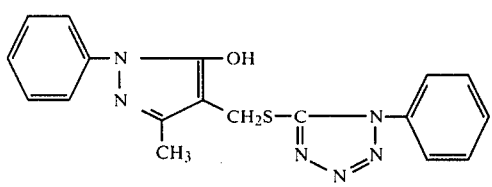
(1)
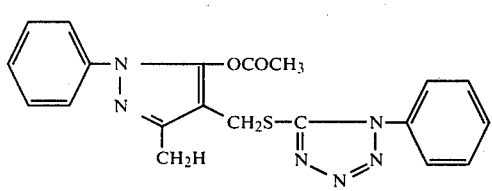
(2)
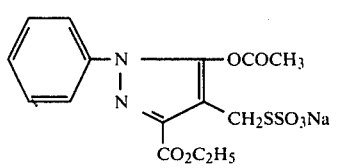
(3)
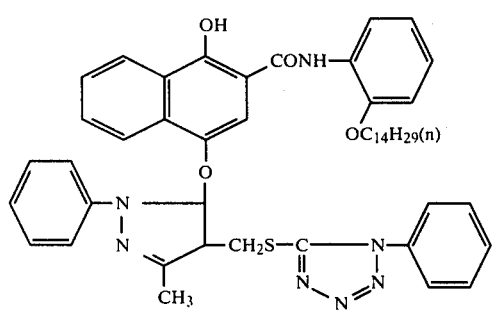
(4)
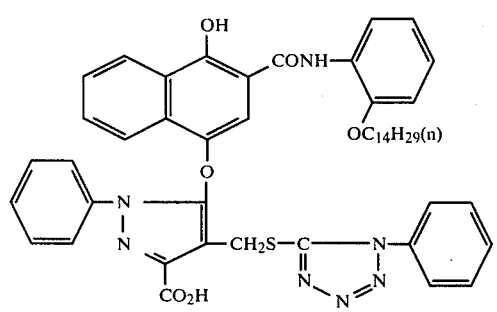
(5)
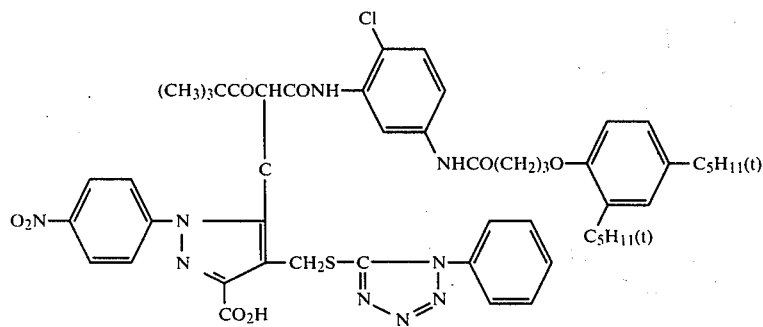
(6)

-continued
(7)
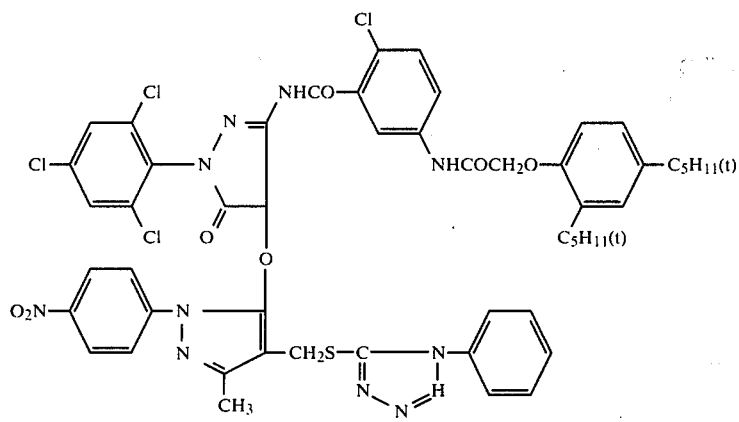
(8)
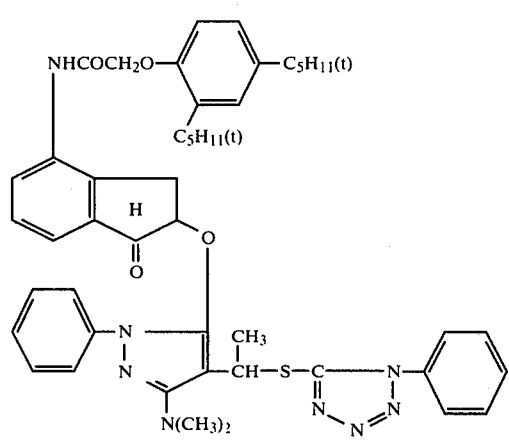
(9)
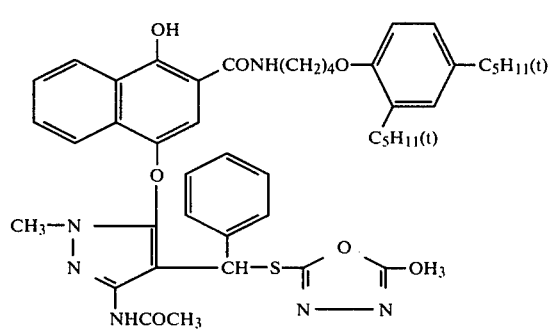
(10)
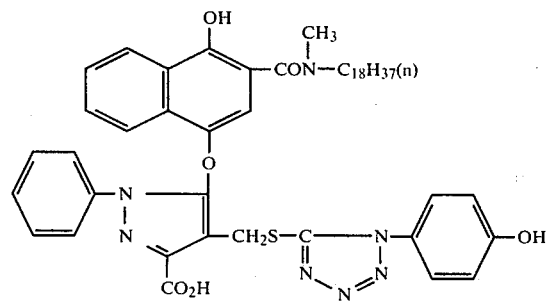

(11)
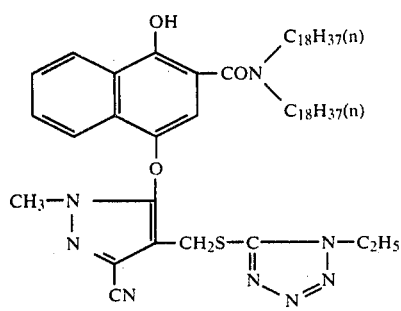
(12)
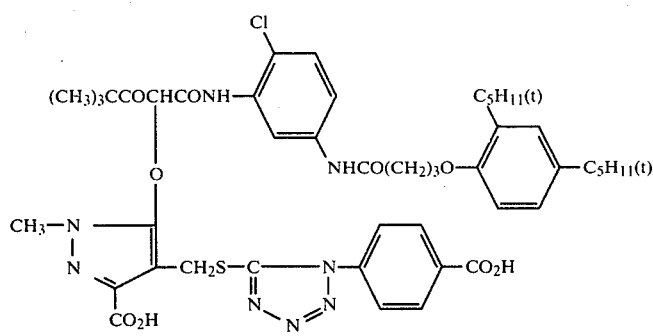
(13)
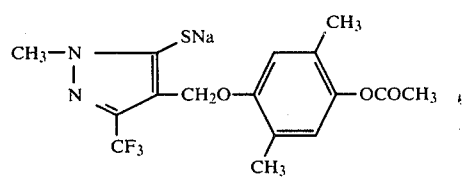
(14)
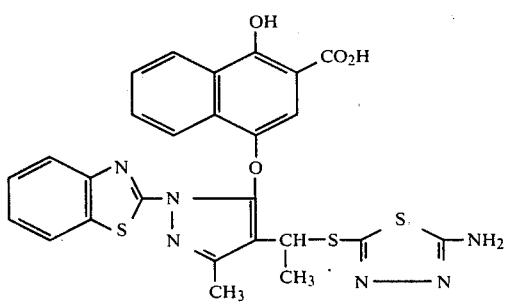
(15)
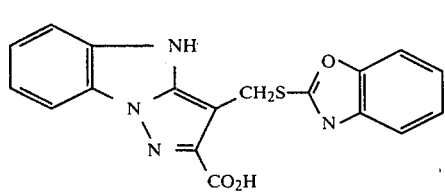
(16)
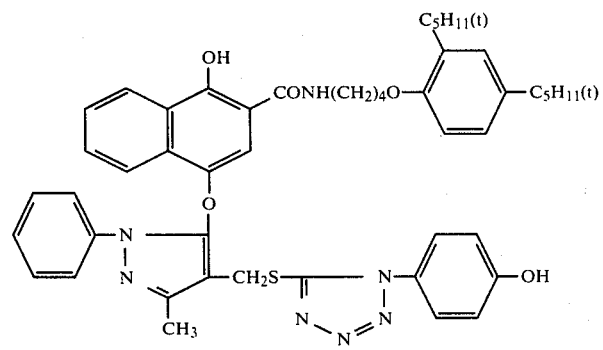

-continued
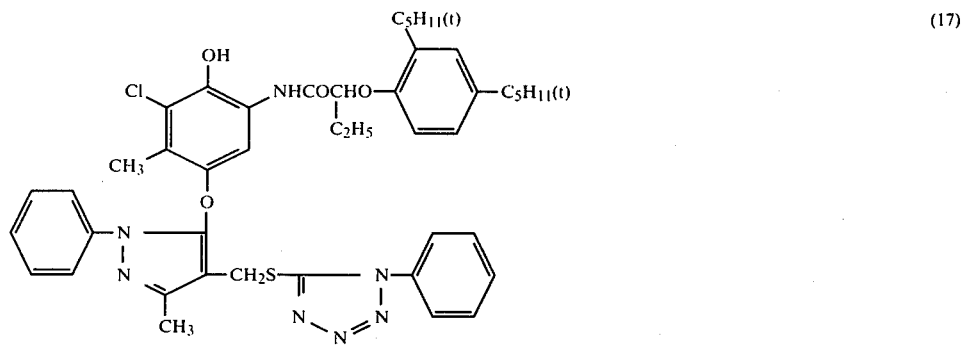
(17)
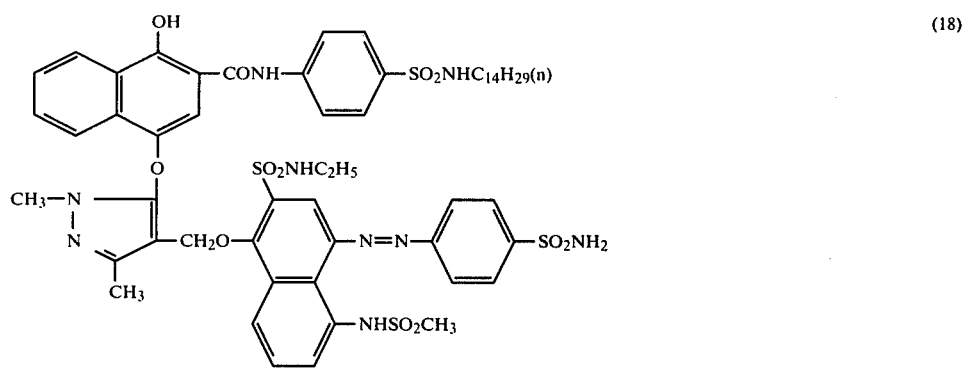
(18)
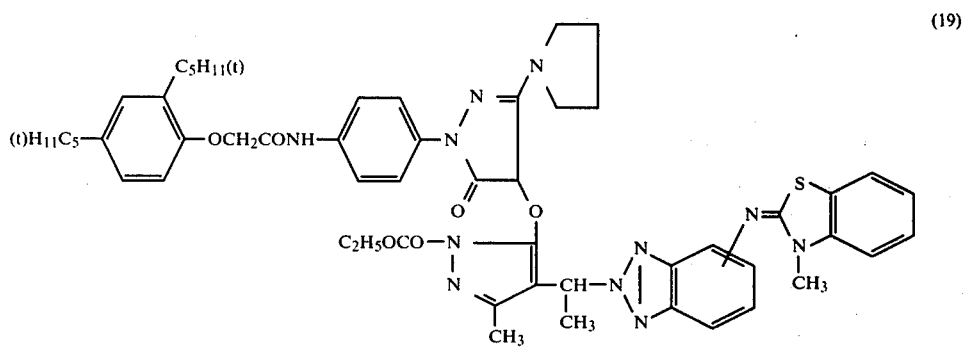
(19)
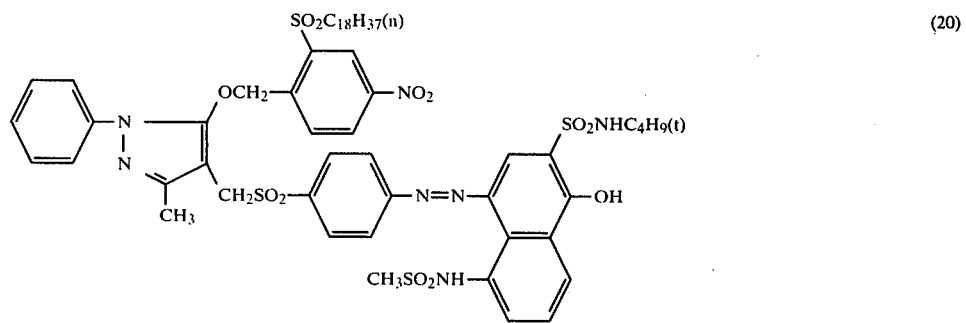
(20)

-continued
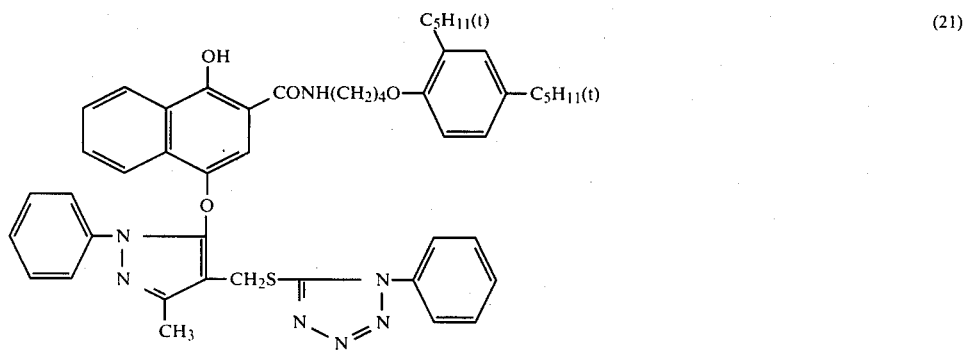
(21)
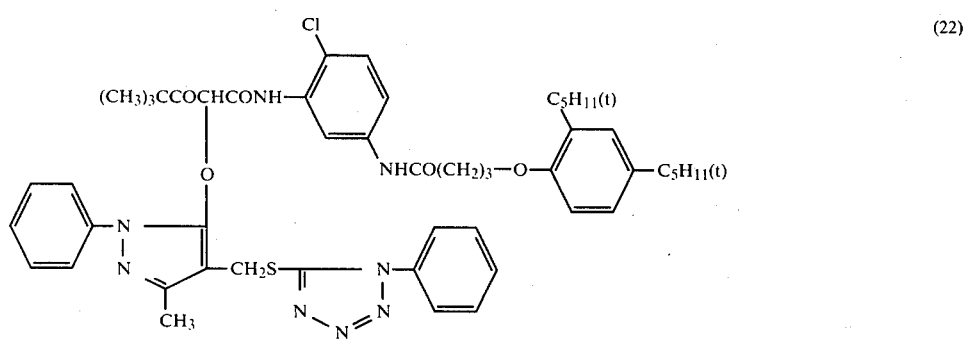
(22)
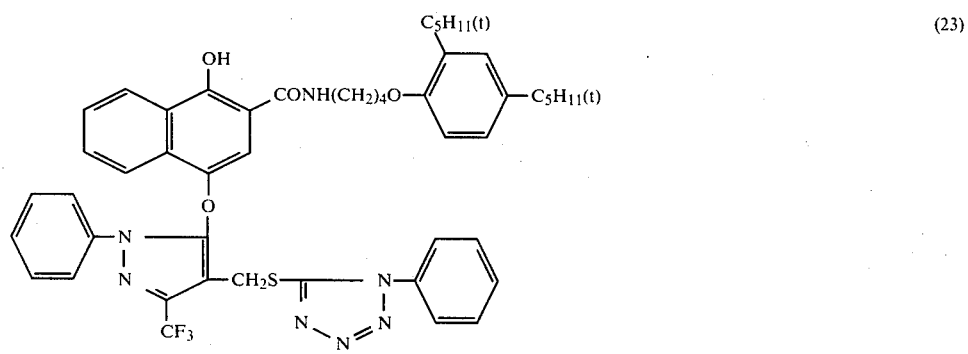
(23)
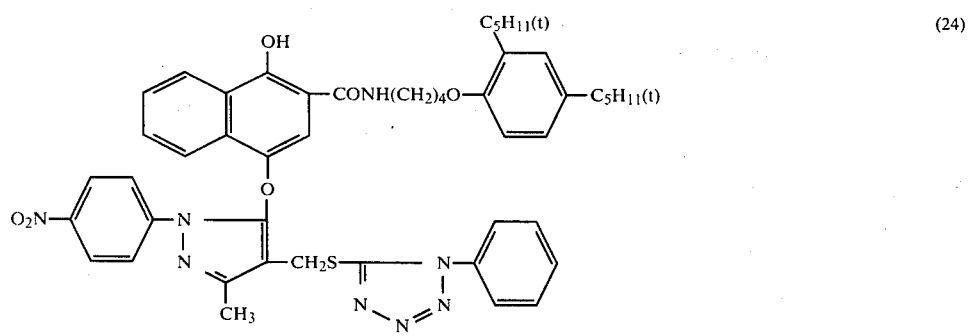
(24)

-continued
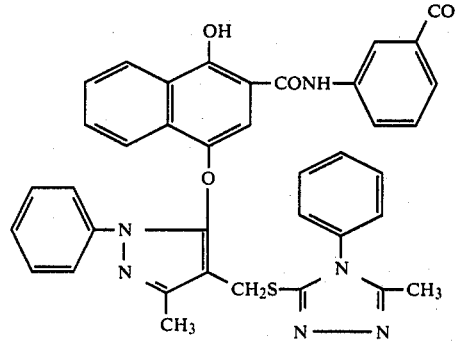
(25)
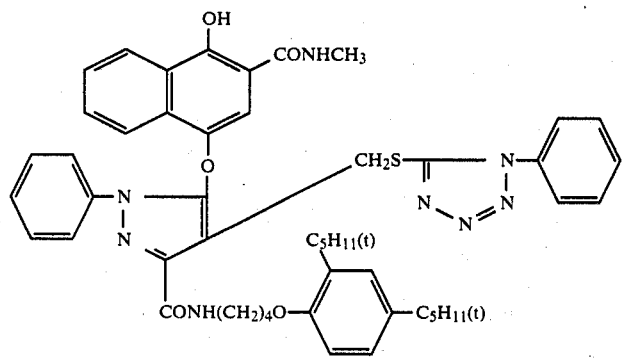
(26)
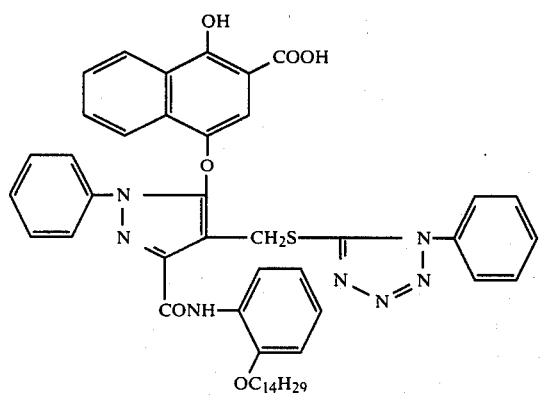
(27)
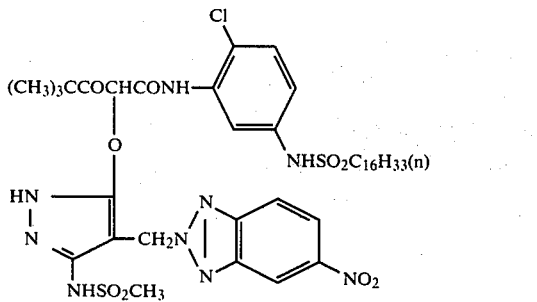
(28)
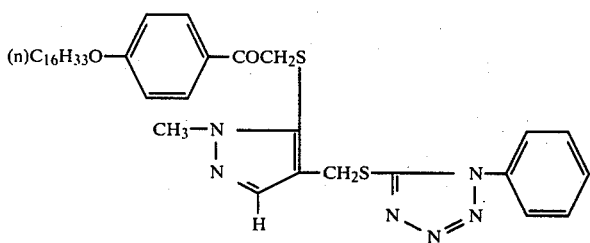
(29)

-continued
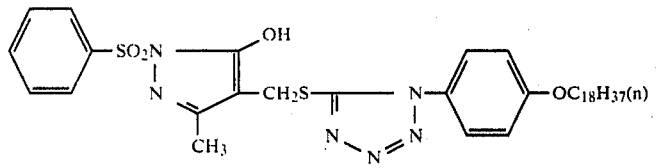 (30)
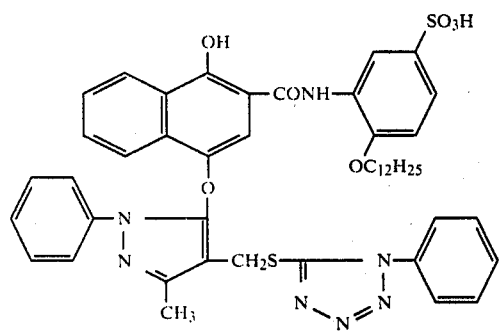 (31)
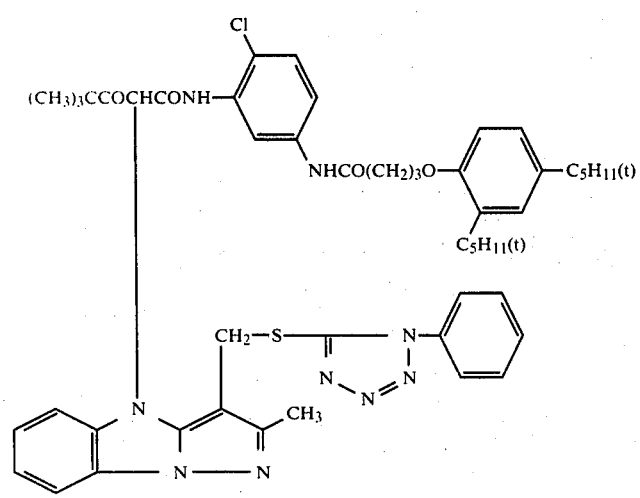 (32)
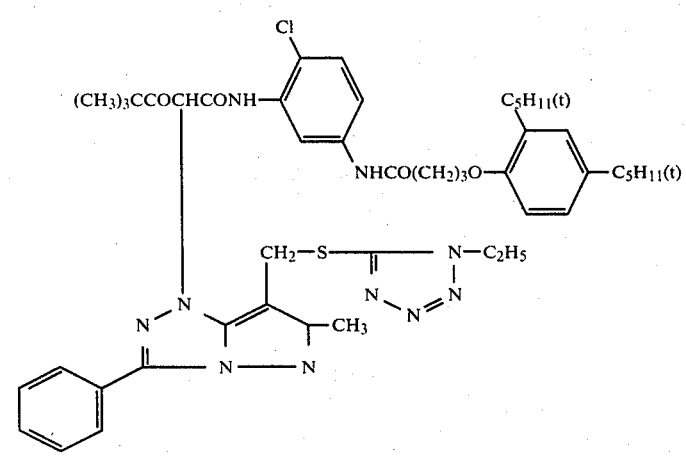 (33)

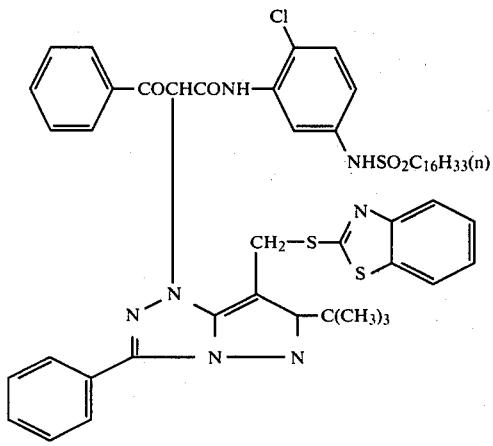

(34)

Synthesis examples of the compounds of the present invention are illustrated below:

Synthesis of Exemplified Compound (4):

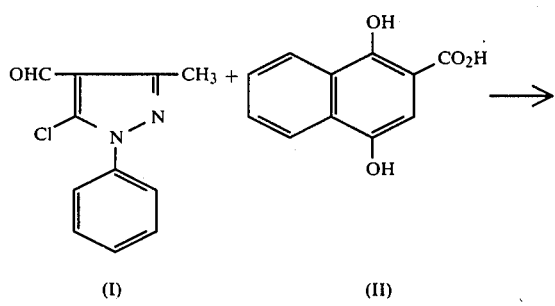

Seven grams of (I) and 6 g of (II) were dissolved into 40 ml of DMF, and to the solution were added 10 ml of solution containing 4 g of NaOH under the atmosphere of N₂, and the resulting solution was kept at the temperature of 80° C. for two hours. The reaction liquid was poured into a dilute hydrochloric acid to deposit crystals, which were filtered, washed and then dried, whereby 11 g of (III) were obtained.

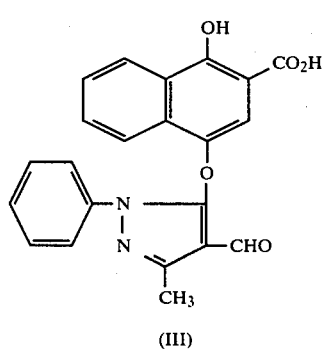

Ten grams of (III) were dissolved into 20 mg of DMSO, and to the solution were added slowly 1.5 g of NaBH₄ at room temperature, and then the solution was allowed to stand for one hours. The reaction liquid was poured into a dilute hydrochloric acid to deposit crystals, which were filtered, washed with ethyl acetate, and then dried, whereby 9 g of (IV) were obtained. mp 214° C.

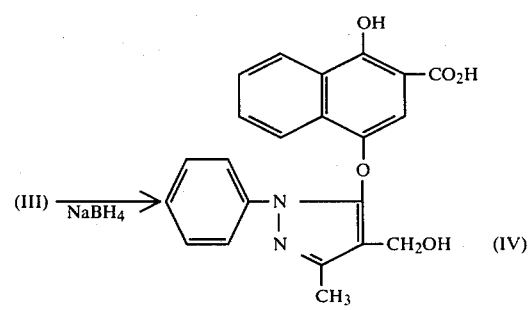

Eight grams of (IV) were added to 8 ml of PCl₃ to be dissolved therein and the solution was then solidified, to which were added 30 ml of acetone and ice. The resulting crystals were washed and filtered, thereby obtaining 5 g of (V). mp 185° C.

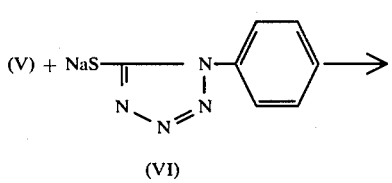

-continued

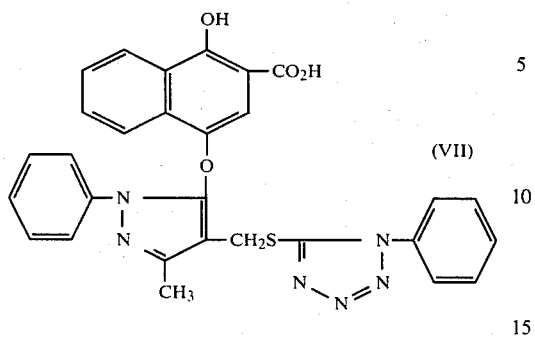

Five grams of (V) and 25 g of (VI) were dissolved into 20 ml of DMF and then the solution was allowed to stand for one hour at room temperature. The reaction liquid was poured into a dilute hydrochloric acid to deposit crystals, which were then filtered. The crystals were extracted, using ethyl acetate and an aqueous K₂CO₃ solution, and the ethyl acetate layer was concentrated to botain a resinous product, which was then dissolved into 20 ml of alcohol. The solution, after 1 ml of hydrochloric acid was added thereto, was cooled to thereby produce white crystals, which were filtered and then dried, whereby 6 g of (VII) were obtained. mp 205° C.

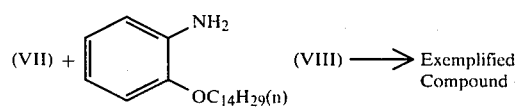

Six grams of (VII) and 3 g of (VIII) were dissolved into 30 ml of dioxane, and to the solution were added 2.5 g of dicyclocarbodiimide, and the resulting solution was allowed to stand at room temperature over a period of 8 hours. The resulting crystals were filtered off, and the filtrate was concentrated to obtain a resinous product, which was then recystallized, using benzene and hexane, whereby 4.5 g of Exemplified Compound (4) were obtained. mp 105°–105.5° C. The product was ascertained by NMR and mass spectrometry.

Synthesis of Exemplified Compound (21):

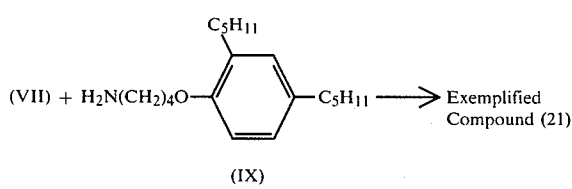

Six grams of (VII) and 3 g of (IX) were dissolved into 20 ml of dioxane, and to the solution were added 2.5 g of dicyclocarbodiimide, and the mixture was allowed to stand at room temperature over a period of 8 hours. The resulting crystals were filtered off, and the filtrate, after being concentrated to become resinous, was recrystalized in ligroin, whereby 5 g of Exemplified Compound (21). mp 136°–137° C. The compound was ascertained by NMR and mass spectrometry.

Synthesis of Exemplified Compound (5):

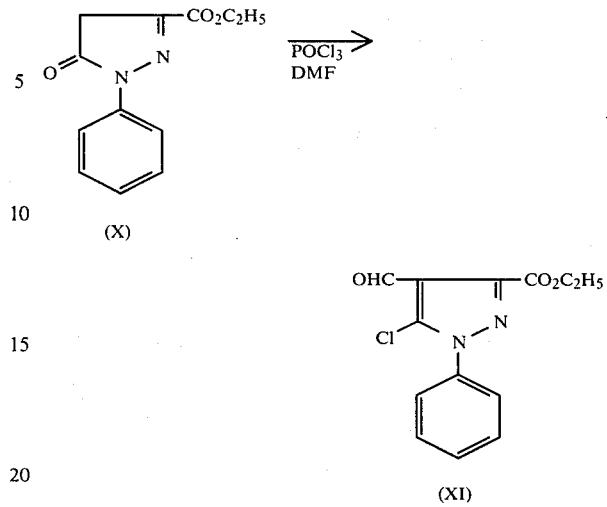

150 milliliters of DMF were cooled by ice, into which were poured 65 ml of POCl₃ kept at a temperature not more than 20° C. Ten minutes later, 120 g of (X) were slowly added to the mixture, which was then allowed to stand at 60° C. for one hour, to which were further added 130 ml of POCl₃. The mixture was subequently refluxed for one hour. The reaction liquid was poured into ice, and the thus produced crystals were filtered and recrystallized in ethyl acetate. mp 141° C.

After that, in a similar manner to that in the synthesis of Exemplified Compound (4), (XII) was obtained. mp 45° C.

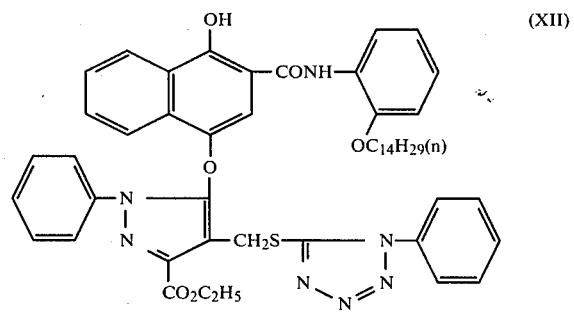

Six grams of (XII) were dissolved into a mixture of 20 ml of methanol with 4 ml of an aqueous solution containing 2 g of NaOH, and the mixed solution was allowed to stand at room temperature for four hours. The reaction liquid was poured into a silute hydrochloric acid, and the resulting crystals were filtered, dried and then recrystallized in acetonitrile. mp 54°–58° C. The product was ascertained by NMR and mass spectrometry.

These compounds of the present invention may be incorporated into silver halide photographic light-sensitive material in a manner well known to those skilled in the art. The adding amount may be varied according to purposes and is approximately from 0.001 to 1 mole per mole of silver halide.

The compounds of the present invention may be used together with those various additives usually used in silver halide photographic light-sensitive materials and may also be used in combination of not less than two kinds thereof. The addition of the compounds of the present invention may be made either to the layer containing silver halide or to a different layer of a light-sensitive material.

The compounds of the present invention permit the control of artitrary elimination of PUG with respect to timing and distance, i.e., the compounds are conspicuous in the so-called interlayer effect thereof.

The present invention is illustrated with reference to examples below, but the present invention is not limited thereto.

EXAMPLE 1

On a subcoated cellulose triacetate film support an emulsion layer was coated and then dried, the emulsion being prepared in the manner that 10.6 g of a cyan coupler 1-hydroxy-N-[4-(2,4-di-tert-amyl-phenoxy)-butyl]-2-naphthoamide were dissolved into a mixture of 11 ml of tricresyl phosphate with 30 ml of ethyl acetate, and this was mixed with 20 ml of a 10% aqueous Alkanol B (alkyl-naphthalene sulfonate, manufactured by DuPont) solution and 200 ml of a 5% aqueous gelatin solution, and the resulting mixture was emulsified and dispersed by means of a colloid mill to obtain an emulsion, which dispersed liquid was added to 1 kg of a red-sensitive silver iodobromide emulsion (containing 6 mol % silver iodide) and to the emulsion were further added 40 ml of a 2% aqueous solution of 1,2-bis(vinyl sulfonyl) ethane as a hardener. (The coated amount of silver: 12 mg/100 cm$^2$; molar ratio of coupler/Ag=0.1)

The thus obtained silver halide color photographic light-sensitive material is regarded as sample (1).

Those prepared by incorporating Exemplified compounds (4) and (22) into the emulsion layer used in sample (1) are regarded as sample (2) and sample (3), respectively. And those prepared by incorporating the following control compounds (1) and (2) into the emulsion layer of sample (1) are regarded as sample (4) and sample (5), respectively.

Control Compound (1)

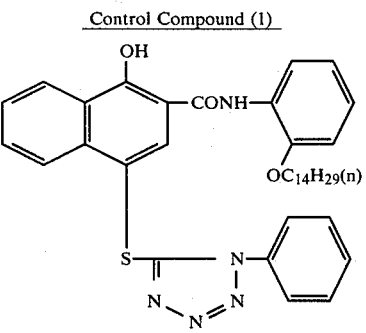

Control Compound (2)

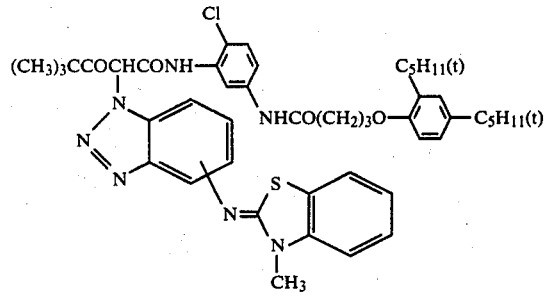

These samples, after being exposed through an optical wedge with an intensity scale sensitometer, were subjected to a color development in accordance with the following processing steps to thereby obtain the results as shown in Table 1.

| Processing Steps (at 38° C.): | Processing time |
| --- | --- |
| Color developing | 3 min. 15 sec. |
| Bleaching | 1 min. 30 sec. |
| Washing | 3 min. 15 sec. |
| Fixing | 6 min. 30 sec. |
| Washing | 3 min. 15 sec. |
| Stabilizing | 1 min. 30 sec. |

The processing compositions used in the steps are as follows:

| Color Developer Composition: | |
| --- | --- |
| 4-amino-3-methyl-N—ethyl-N—(β-hydroxyethyl)-aniline sulfate | 4.75 g |
| Anhydrous sodium sulfite | 4.25 g |
| Hydroxyamine ½ sulfate | 2.0 g |
| Anhydrous potassium carbonate | 37.5 g |
| Sodium bromide | 1.3 g |
| Trisodium nitrilotriacetate, monohydrated | 2.5 g |
| Potassium hydroxide | 1.0 g |
| Water to make 1 liter | |

The pH is adjusted to be 10.0 by use of potassium hydroxide.

| Bleaching solution composition: | |
| --- | --- |
| Iron-ammonium ethylenediamine tetra-acetate | 100.0 g |
| Diammonium ethylenediamine tetra-acetate | 10.0 g |
| Ammonium bromide | 150.0 g |
| Glacial acetic acid | 10.0 ml |
| Water to make 1 liter | |

The ph is adjusted to be 6.0 by use of aqueous ammonia.

| Fixing solution composition: | |
| --- | --- |
| Ammonium thiosulfate (50% aqueous solution) | 162.0 mg |
| Anhydrous sodium sulfite | 12.4 g |
| Water to make 1 liter | |

The pH is adjusted to be 6.5 by use of acetic acid.

| Stabilizing solution composition: | |
|---|---|
| Formalin (37% aqueous solution) | 5.0 ml |
| Koniducks (manufactured by Konishiroku Photo Industry Co., Ltd.) | 7.5 ml |
| Water to make 1 liter | |

TABLE 1

| Sample No. | Compound | Adding amount (mol/Ag mol × 100) | Speed | Gamma | Fog |
|---|---|---|---|---|---|
| 1 | Blank | — | 100 | 1.50 | 0.26 |
| 2 | Exemplified compound (4) | 0.1 mol % | 85 | 0.95 | 0.18 |
|   |   | 0.4 mol % | 45 | 0.55 | 0.10 |
| 3 | Exemplified compound (22) | 0.15 mol % | 90 | 0.98 | 0.21 |
|   |   | 0.6 mol % | 65 | 0.65 | 0.15 |
| 4 | Control compound (1) | 0.2 mol % | 88 | 1.14 | 0.22 |
|   |   | 0.8 mol % | 71 | 0.75 | 0.16 |
| 5 | Control compound (2) | 0.2 mol % | 84 | 0.97 | 0.25 |
|   |   | 0.8 mol % | 63 | 0.77 | 0.15 |

The same samples, after being allowed to stand in the atmospheric condition of 60° C. with 80%RH for two days (aging treatment), were exposed concurrently and then subjected to similar processings. The results are as shown in Table 2.

TABLE 2

| Sample No. | Compound | Adding amount (mol/Ag mol × 100) | Speed | Gamma | Fog |
|---|---|---|---|---|---|
| 1 | Blank | — | 90 | 1.24 | 0.28 |
| 2 | Exemplified compound (4) | 0.1 mol % | 85 | 0.90 | 0.20 |
|   |   | 0.4 mol % | 44 | 0.77 | 0.11 |
| 3 | Exemplified compound (22) | 0.15 mol % | 88 | 0.86 | 0.23 |
|   |   | 0.6 mol % | 64 | 0.72 | 0.14 |
| 4 | Control compound (1) | 0.2 mol % | 80 | 0.76 | 0.25 |
|   |   | 0.8 mol % | 68 | 0.45 | 0.20 |
| 5 | Control compound (2) | 0.2 mol % | 64 | 0.88 | 0.30 |
|   |   | 0.8 mol % | 55 | 0.65 | 0.24 |

As apparent from Table 1 and Table 2, it is understood that the compounds of the present invention enables the control of gamma with small amounts thereof as compared to conventional DIR couplers and are so stable that they showed little or no change in their functions even after being subjected to the condition of 60° C. with 80%RH over a period of two days.

EXAMPLE 2

On an antihalation layer-having triacetate film base a silver halide emulsion layer was coated and dried, the emulsion layer being prepared in the manner that 15 g of a magenta coupler 1-(2,4,6-trichlorophenyl)-3-[3-(2,4-di-tert-amylphenoxyacetanilide)benzamide]-5-pyrazolone were dissolved into a mixture of 15 g of tricresyl phosphate with 45 ml of ethyl acetate to obtain an emulsion in the same way as in Example 1, and the thus obtained dispersion liquid was added to 1 kg of a green-sensitive silver iodobromide emulsion (containing 6 mol% silver iodide), to which was further added the same hardener as in Example 1.

The thus obtained silver halide color photographic light-sensitive material is regarded as sample (6). Those prepared by incorporating Exemplified compounds (5) and (21) of the present invention into the emulsion layer of sample (6) are regarded as sample (7) and sample (8), respectively. And those prepared by incorporating the following control compounds (3) and (4) described in Japanese Patent O.P.I. Publication No. 145135/1979 to sample (6) are regarded as sample (9) and sample (10), respectively.

The above-described samples were exposed and processed in similar manner to those in Example 1. And they were also subjected to aging treatments followed by exposure and processing in similar manners like Example 1. The results are shown in Table 3.

Control Compound (3):

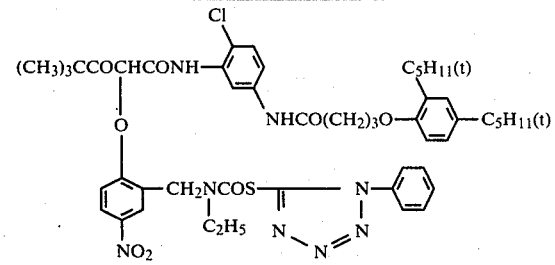

Control Compound (4):

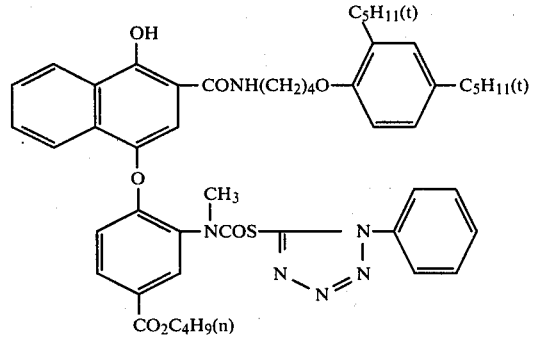

With respect to the sharpness, MTF (Modulation Transfer Function) values in a green light were found for the comparison between the values in spatial frequencies of 10 lines/mm and 30 lines/mm.

TABLE 3

| Sample No. | Compound | Adding amount (mol/Ag mol × 100) | Speed | Gamma | MTF 10 lines/mm | MTF 30 lines/mm |
|---|---|---|---|---|---|---|
| 6 | Blank | — | 95 | 93 | 84 | 59 |
| 7 | Exemplified compound (5) | 0.1 mol % | 96 | 92 | 135 | 88 |
| 8 | Exemplified compound (21) | 0.5 mol % | 94 | 93 | 129 | 84 |
| 9 | Control compound (3) | 0.3 mol % | 87 | 84 | 118 | 74 |
| 10 | Control compound (4) | 0.2 mol % | 92 | 89 | 121 | 78 |

The values of the emulsion speed and gamma are shown in the equivalent of $$\frac{\text{the value with aging treatment}}{\text{the value without aging treatment}} \times 100.$$

The values of MTF is those in the case that none of samples were subject to an aging treatment. The adding amounts are varied according to the respective compounds used so that the gamma values are on an approximately same level.

As shown in Table 3, it is understood that the compounds of the present invention are excellent in the stability in storage as compared to those described in Japanese Patent O.P.I. Publication No. 145135/1979 and contribute to the improvement in sharpness.

EXAMPLE 3

A transparent triacetate base was coated thereon with the following layers in the order described below:
1st layer: The same red-sensitive emulsion as used in Example 1 was coated and dried.
2nd layer: A gelatin interlayer containing 0.5 g/m² of gelatin and 0.1 g/m² of 2,5-tert-octyl hydroquinone.
3rd layer: The same green-sensitive emulsion as used in Example 2 was coated and dried.
4th layer: A protective layer containing 0.5 g/m² of gelatin.

The thus obtained sample is regarded as sample (11). Those prepared by incorporating the compounds as DIR compounds as shown in Table 4 into the oily component of the 3rd layer of sample (11) are regarded as samples (12), (13), (14), (15), (16) and (17), respectively.

The thus obtained samples, after being exposed through an optical wedge to a green light, were further uniformly exposed to a red light only with an exposure so that the red density becomes 2.0, and then subjected to similar processings to those in Example 1, and the results are shown in Table 4.

In addition, the IIE (Interimage Effect) in Table 4 were found in the following manner. The red-sensitive layer is in itself uniformly exposed so that the density thereof becomes equal to 2.0, but the development of the red-sensitive layer is inhibited due to the IIE according to the density developed in the green-sensitive layer; that is, according to the inhibitor released, and thus the red density becomes reduced (this reduced density in red density as $D_1$); such reducing degree of the red density was found as IIE in the following formula:

$$IIE = \frac{2.0 - D_1}{2.0} \times 100$$

Therefore, the greater the value obtained the stronger the interimage effect and the more is the color reproduction improved.

TABLE 4

| Sample No. | Compound | Adding amount (mol/Ag mol × 100) | Gamma of Green-sensitive layer | IIE (%) |
|---|---|---|---|---|
| 11 | Blank | — | 1.32 | 4 |
| 12 | Exemplified compound (16) | 0.6 mol % | 0.85 | 28 |
| 13 | Exemplified compound (23) | 0.5 mol % | 0.88 | 21 |
| 14 | Exemplified compound (24) | 0.6 mol % | 0.81 | 15 |
| 15 | Control compound (1) | 0.5 mol % | 0.87 | 8 |

TABLE 4-continued

| Sample No. | Compound | Adding amount (mol/Ag mol × 100) | Gamma of Green-sensitive layer | IIE (%) |
|---|---|---|---|---|
| 16 | Control compound (2) | 0.5 mol % | 0.84 | 13 |
| 17 | Control compound (4) | 0.2 mol % | 0.89 | 7 |

As seen from Table 4, the compounds of the present invention have great interimage effects and are effective for the reproduction of color.

Similar results were obtained when the above examples were applied to the so-called false color system which is such that the wavelength region to which an emulsion layer is sensitive is not in complementary color relation with the absorption wavelength of the dye formed from the coupler contained in the emulsion layer.

EXAMPLE 4

Those prepared by incorporating Exemplified compound (2) and the following compound in the following adding amount into sample (1) which was used in Example 1 are regarded as sample (18) and sample (19), respectively.

Control Compound (5), the compound described in Japanese Patent Examined Publication No. 39727/1979:

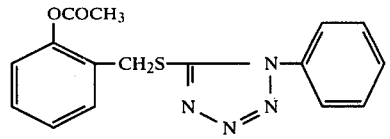

These samples were exposed and processed in accordance with Example 1, and the results are shown in Table 5, while the results obtained after the accelerated aging of the samples are shown in Table 6.

TABLE 5

| Sample No. | Compound | Adding amount (mol/Ag mol × 100) | Speed | Max. density of color formed | Fog |
|---|---|---|---|---|---|
| 1 | Blank | — | 100 | 1.90 | 0.26 |
| 18 | Exemplified compound (2) | 0.2 mol % | 80 | 1.20 | 0.18 |
| 19 | Control compound (5) | 0.2 mol % | 92 | 1.81 | 0.24 |

TABLE 6

| Sample No. | Compound | Adding amount (mol/Ag mol × 100) | Speed | Max. density of color formed | Fog |
|---|---|---|---|---|---|
| 1 | Blank | — | 95 | 1.75 | 0.28 |
| 18 | Exemplified compound (2) | 0.2 mol % | 87 | 1.16 | 0.20 |
| 19 | Control compound (5) | 0.2 mol % | 74 | 1.33 | 0.18 |

As seen from Tables 5 and 6, the compound of the present invention has higher development inhibitor releasing rate in the processing condition as compared to the compound described in Japanese Patent Examined Publication No. 39727/1979 and is excellent in the stability in storage.

EXAMPLE 5

Ten milligrams of Exemplified Compound (20) of the present invention and 5 mg of 2,5-di-(tert)-octyl hydroquinone were dissolved into 5 ml of ethyl acetate, and the resulting solution was vigorously shaken together with 5 ml of 1 N aqueous sodium hydroxide solution in a test tube, and after that the tube was left as it was, then a magenta dye was observed appearing in the solution.

This is considered because the compound of the present invention has released the dye in the photographic reduction condition.

What is claimed is:

1. A silver halide photographic light-sensitive material which comprises at least one of those pyrazole compounds represented by the following general formula:

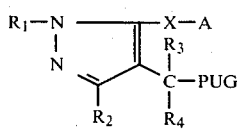

wherein A is a group which can be eliminated in a photographic process condition; X is

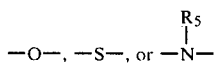

wherein $R_5$ is a hydrogen atom or an alkyl, an aryl, an acyl or a sulfone group, which $R_5$ group may combine together with $R_1$ to form a condensed ring; $R_1$ is a hydrogen atom or an alkyl, an aryl, an acyl, a sulfone, an alkoxy, or a heterocyclic residue; $R_2$ is a hydrogen atom or an alkyl, an aryl, an alkoxy, an amino, an acid amide, a sulfonamide, a carboxyl, an alkoxycarbonyl, a carbamoyl, a cyano, or a halogenated alkyl group, $R_3$ and $R_4$ each is a hydrogen atom or an alkyl or an aryl group; and PUG is a photographically useful group which is released after elimination of the A group in a photographic processing condition and which has a hetero atom directly combined with the carbon substituted in the fourth position of the pyrazole nucleus.

2. A silver halide photographic light-sensitive material according to claim 1, wherein A is a group which can be eliminated in an alkaline processing solution.

3. A silver halide photographic light-sensitive material according to claim 1, wherein A is selected from the group consisting of a hydrogen atom, a metal atom, an acyl group, a sulfonyl group and a coupler residue.

4. A silver halide photographic light-sensitive material according to claim 1, wherein PUG is a group selected from the group consisting of a development inhibitor residue, a bleach restrainer residue, a silver halide solvent residue, a photographic dye residue, and a coupler residue.

5. A silver halide photographic light-sensitive material according to claim 3, the coupler residue is a benzoyl acetanilide type yellow coupler residue, a pivaloyl acetanilide type yellow coupler residue, a pyrazolone magenta coupler residue, an indazolone magenta coupler residue, a phenol cyan coupler residue or a naphtol cyan coupler residue.

6. A silver halide photographic light-sensitive material according to claim 1, wherein A is a coupler residue and PUG is a development inhibitor residue.

* * * * *